United States Patent [19]

Potts

[11] Patent Number: 5,382,436
[45] Date of Patent: Jan. 17, 1995

[54] CAFFEINE IN THE TREATMENT OF HERPES SIMPLEX VIRUS INFECTIONS

[75] Inventor: Michael Potts, Moreton in Marsh, United Kingdom

[73] Assignee: Surtech International Limited, United Kingdom

[21] Appl. No.: 849,447

[22] PCT Filed: Nov. 23, 1990

[86] PCT No.: PCT/GB90/01819
§ 371 Date: Jul. 23, 1992
§ 102(e) Date: Jul. 23, 1992

[87] PCT Pub. No.: WO91/07969
PCT Pub. Date: Jun. 13, 1991

[30] Foreign Application Priority Data

Nov. 24, 1989 [GB] United Kingdom ............. 8926595

[51] Int. Cl.$^6$ ............................................. A61K 31/52
[52] U.S. Cl. .............................. 424/489; 424/DIG. 5; 424/64; 424/445; 424/195.1; 514/934; 514/944; 514/951
[58] Field of Search ............. 424/DIG. 5, 195.1, 489, 424/64; 514/263, 934, 264; A61K 31/52

[56] References Cited

U.S. PATENT DOCUMENTS

| | | | |
|---|---|---|---|
| 4,132,782 | 1/1979 | Bean | 424/195.1 |
| 4,684,522 | 8/1987 | Marissal et al. | 424/195.1 |
| 4,945,094 | 7/1990 | Salim | 514/264 |
| 5,030,451 | 7/1991 | Trebosc et al. | 424/401 |

OTHER PUBLICATIONS

Chemical Abstracts, vol. 109, No. 25, 19 Dec. 1988, W. P. P. Leary et al., Xanthines in Treatment of Herpes Blisters, p. 72.

Primary Examiner—Thurman K. Page
Assistant Examiner—James M. Spear
Attorney, Agent, or Firm—Kirschstein, et al.

[57] ABSTRACT

Pharmaceutical compositions for topical use in the treatment of infections caused by Herpes virus comprising from 8 to 12% caffeine as active ingredient and a pharmaceutically acceptable topical excipient, the caffeine particles being less than 50 μm in size or having a particle size distribution in which at least 90% of the particles have a mass median diameter of less than 9 μm. Methods of treating patients suffering from Herpes infections in a tissue area, comprising topical application of the novel compositions, are also disclosed.

9 Claims, No Drawings

CAFFEINE IN THE TREATMENT OF HERPES SIMPLEX VIRUS INFECTIONS

BACKGROUND OF THE INVENTION

This invention relates to pharmaceutical compositions for use in the treatment of lesions resulting from Herpes Simplex Virus (HSV) infections.

Herpes simplex is an enveloped, Class I Double Stranded DNA Virus. It infects vertebrates and it is thought that by the age 21, up to 80% of the population are infected with the so-called Type I virus or Herpes simplex labialis hereinafter referred to as HSVI. The vital infection begins when a virion comes into contact with a host cell and attaches to it. The vital DNA and proteins then cross the membrane into the cytoplasm of the cell ending up in the nucleus where the vital nucleic acid interacts with the host cell's nucleic acid synthesising machinery to direct its own replication and the synthesis of vital proteins. The multiple components of the herpes virions assemble in stages resulting in the production of a new round of virus particles and the death of the cell.

Primary HSVI infection occurs normally as a result of direct mouth to mouth or hand to mouth contact with a carrier. The primary infection is widespread (e.g. a rash inside the mouth) and often goes unnoticed. Following infection, the virus particles travel by axonal flow to nerve ganglia within the maxillary branch of the trigeminal nerve (which supplies the muscles around the mouth) where they remain dormant.

The dormant virus can undergo reactivation at any time resulting in localized lesions—the characteristic "cold-sore". Reactivation factors include any occurences causing immunosuppression such as infection, stress, pregnancy, drugs etc.

The second strain of HSV is HSV II—(Herpes simplex genitalis) which give rise to lesions in the genital regions. HSV II is sexually transmitted and although HSV types I and II were originally separate they have become interchangeable due to aberrant sexual practices.

Infants can become infected with HSV II as a result of passage through the birth canal of an infected mother. Following infection with HSV II the virus remains dormant in the sacral ganglia.

A current treatment for HSV infections is use of the drug Acyclovir which acts to prevent viral replication by blocking the action of the vital DNA polymerase. Though very effective, this drug is expensive, available only on prescription, and is generally recommended for use only under close medical supervision.

SUMMARY OF THE INVENTION

An object of this invention is to provide a pharmaceutical composition in a form which can be applied topically for the treatment of lesions resulting from HSV infections which is less expensive than Acyclovir and is available without prescription.

Methyl xanthines such as caffeine, theophylline and theobromine have been shown to have an inhibitory effect in vitro on the growth of Hela, Veto and human diploid skin fibroblasts in tissue culture (Lino et al., 1976. Shaw et al., 1981). These authors have described inhibitory effects on proliferation at concentrations about 4 mM. Damon and Raouth (1969) found that caffeine inhibits or delays mitosis in mouse L cells and at a concentration of 2 mM causes a delay in progression of cells in the $G_1$ phase of growth to the S phase where cells are engaged in DNA synthesis. Beetham and Tolmach (1982) working with Hela cells, found that caffeine at concentrations below 15 mM kills only cells replicating DNA. That caffeine suppresses the growth of certain viruses including polio, influenza and vaccinia virus but has no effect on JEV or NDV has been demonstrated by Yamoviaki and Tagaya (1980).

It has further been suggested (Morgan et al., (1968), Smith (1964) and Nil et al., (1968)) that caffeine may act to prevent proper assembly of the virion in the nucleus namely be disrupting the budding process through the nuclear membrane so that those particles which do bud through the membrane collect malformed envelopes and are rendered non-infective.

None of these prior art references discloses or suggests that caffeine might possess anti-vital activity when administered topically to cells infected with HSV, nor has it ever been demonstrated hitherto that the topical administration of a specific caffeine-containing formulation at a defined stage in the infective cycle has a therapeutic effect in treating infections.

We have now carried out experiments which demonstrate that caffeine has an inhibitory effect on the replication of HSV. More importantly, it has been shown that in Hela, Veto and skin fibroblast cells the titre of HSVI is reduced to 99% on treatment with 8 mM caffeine whilst 2 mM led to an 87% reduction and that HSV II is similarly inhibited. At 4 mM of caffeine HSV inhibition was optimal when compared to the likely toxic effects at higher doses on the cells themselves. Following from these findings, the therapeutic efficacy of certain caffeine-containing formulations has been demonstrated and specific formulation classes identified in which the therapeutic effectiveness is particularly high.

According to the present invention there are provided pharmaceutical compositions for topical use in the treatment of infections with Herpes simplex virus comprising as active ingredient an effective concentration of caffeine and a pharmaceutically acceptable excipient suitable for topical administration.

Most preferably the caffeine is in micronised form, i.e. with a particle size distribution such that substantially all of the particles are less than 50 μm and preferably less than 20 μm in size. Most preferably at least 90% of the particles are less than 9 μm in size and have an MMD (mass median diameter) of less than 10, preferably 4 to 8 μm.

The excipients are preferably selected so as to promote local retention of the active ingredient.

In particularly effective compositions the excipients include at least one lipophillic material. Suitable lipophillic materials include high Mw (e.g. $C_{12-24}$) paraffins and mixtures thereof, higher ($C_{12+}$) alcohols, natural fats, e.g. glycerol esters of $C_{13}$–$C_{24}$ carboxylic acids including saturated FAs such as stearic acid and unsaturated FAs such as oleic acid.

Other specific lipophillic excipients include paraffin waxes, petroleum jelly and cocoa butter.

Further ingredients which may be included are: emulsifying agents, buffering reagents, stabilisers, preservatives and colouring, perfuming and flavouring agents.

DETAILED DESCRIPTION OF EXPERIMENTS

The following experiments were carried out to assess the anti-HSV effect of caffeine:

1. Anti-HSV Effects of Caffeine In Vitro

The growth of HSVI in Hela cells with and without caffeine (4 mM) was followed for a period of 42 hours. In the presence of caffeine, virus yield was always lower than that without, the greatest inhibition being seen after 12 hours.

To determine at what stage in the course of the virus replicative cycle caffeine has an inhibitory effect, caffeine was applied to cultured cells at various times prior to and following infection with HSVI. Provided that caffeine was applied not later than 12 hours post infection, the vital yield was always lower—the greatest inhibition being observed when caffeine was administered within the first 4 hours following infection. From these findings it was concluded that caffeine has an inhibitory effect on events early in the infective cycle and our results have shown the drug to specifically inhibit the vital thymidine kinase.

2. Anti-HSV Effect of Caffeine—Clinical Trials

A. A double-blind protocol was set up to study the effects of the caffeine formulation when applied to herpetic lesions.

Thirty-two otherwise healthy volunteers who have previously suffered from recurrent herpes labialis were each provided with 2 apparently identical pots of a gel formulation containing either 12.5 g of 10% caffeine or a placebo consisting of caffeine-free gel.

Each was instructed to record on a specially prepared form the date of onset of prodromal symptoms or eruption of lesions and to record severity of symptoms on a 10 cm linear scale.

Application of the gel began immediately that prodromal symptoms occurred or lesions erupted and the gel was applied 4 times daily plus last thing at night.

Swabs were taken daily for vital shedding from a selection of patients starting before the first application of the gel and continuing until vital shedding ceases or the lesions disappear.

Results

Of the volunteers taking part in the trial, 80% were healed within 7 days and 66% reported that the attack was less severe than previous attacks following application of caffeine topically in accordance with the invention and/or the length of time that elapsed until the lesions were completely healed was substantially diminished.

Particularly impressive healing rates were observed when the caffeine was applied during the prodromal stage, immediately after the initial symptoms were first observed. Additionally other symptoms were dramatically reduced.

B. In a second protocol fifty male and female patients between 16 and 65 years of age, with a history of recurrent herpes labialis but who were otherwise normal, healthy volunteers, were recruited from an existing test panel. Subjects with non-herpetic lesions of the lips or adjacent areas of the face who were currently using topical or system medication which was likely to interfere with the study, or who were pregnant or lactating females were excluded from the trial.

The treatments randomly allocated to patients taking part in the trial were as follows:
- 27 patients received caffeine
- 23 patients received base

PROCEDURES

Upon entry into the trial, demographic details and the clinical history of each patient were recorded and the patient was given sufficient gel for 7 days treatment of the lesion. They were asked to record the clinical state of the lesion, treat the skin affected as soon as they had evidence of a return of their cold sore, and to report to the nursing staff as soon as possible. When first reporting with a cold sore, the clinical state of the sore was recorded by the clinician. A diary card was also issued on which the patient could record the progress of the sore on a daily basis.

During the treatment period the patient was instructed to apply gel in 5 evenly spaced applications throughout the day plus at bedtime. The patient was seen after 7 days of treatment, when a reassessment of the cold sore was undertaken and, if necessary, a second 7-day supply of gel and a further diary-card were supplied.

RESULTS

No withdrawals or significant protocol violations occurred. Three patients treated with caffeine gel reported a mild smarting or itching after application but none was severe enough to stop therapy. No other side-effects were noted.

STATISTICAL METHODOLOGY

Summary statistics were employed to compare demographic details of patients allocated to the different treatments.

The data accumulated from the healing and treatment comparisons, clinical assessments, and final evaluation were analysed by nonparametric procedures and/or analysis of variance by ranks whichever being appropriate to the attributes of the data. The diary-card data were categorical and the multi-dimensional tables generated were evaluated by the fitting of log-linear models to the observed frequencies before a fit was accepted, each fitted model had a likelihood ratio$\times 2$ with a p-value $>0.50$. Production of summary tables and the statistical analyses were performed using the computerized statistics packages SYSTAT and GLIM.

Analysis of data related to age, history of cold sores in years, number of cold sores per year, months since the last sore, duration and severity of the last sore showed no statistical differences between the active and base treated groups. Details of the early symptoms together with the clinicians' and patients' assessments of severity of the current cold sore also showed that the two groups did not differ.

Analysis of the time to healing of the study treated cold sores compared to the time to healing of the previous sore showed that caffeine treated sores healed significantly faster than the previous sore ($+=2.748$; $df=25$; $p>0.010$) whereas base treated sores required an equivalent period to heal ($+=0.762$; $df=20$; $p>0.200$).

Statistical analysis of the patients' opinions on the healing of current and last cold sores demonstrated that 61% (14/23) of base treated patients thought their current sore had healed more quickly whilst 73% (19/26) of the caffeine treated patients made a similar claim, a difference which is regarded as being clinically meaningful.

Statistical analysis of data on the clinicians' opinion on how successful the current treatment was showed that whilst 50% (6/12) of base treated patients with comparable current and last sores ("same" or "more severe") were judged to be treatment successes, some 64% (9/14) of the caffeine treated patients were judged similarly, again a difference which is regarded as being clinically meaningful.

DETAILED EXAMPLES OF PHARMACEUTICAL FORMULATIONS

The following examples illustrate the formulation of caffeine into these suitable pharmaceutical forms without however limiting the invention in any way.

Pharmaceutical Formulations

Example 1

Preparation of 5% Caffeine Wax-Based Lipsalve

|  | % |
|---|---|
| (a) | |
| Beeswax - White | 10.000 |
| Candelilla Wax | 15.000 |
| Cetyl Alcohol | 10.000 |
| Eutanol G | 15.000 |
| Citmol 316M | 6.000 |
| Cocoa Butter | 10.000 |
| Propyl Paraben | 0.100 |
| Isopropyl Myristate | 6.000 |
| Shea Butter | 4.000 |
| (b) | |
| Caffeine - micronized (100% <15μ m*) | 5.000 |
| Albalan | 8.000 |
| Water Deionised | 16.000 |
| (c) | |
| Benzoic Acid | 1.000 |

*See Appendix for size distribution

Example 2

Preparation of 10% Caffeine Wax-Based Lipsalve

|  | % |
|---|---|
| (a) | |
| Eutanol G | 16.700 |
| Citmol 316TM | 7.500 |
| Caffeine BP - micronized (100% <15μ m*) | 10.000 |
| Dispex GA40 | 0.200 |
| Isopropyl Myristate | 17.370 |
| (b) | |
| Beeswax - white | 1.500 |
| Candelilla Wax | 16.000 |
| Cetyl Alcohol | 10.000 |
| Cocoa Butter | 12.800 |
| Propyl Paraben | 0.100 |
| Kariderm - Shea Butter | 5.330 |
| Aduvex 24 | 0.500 |
| Parsol MCX | 2.000 |

Example 3

Preparation of 10% Caffeine Adhesive Gel

|  | % |
|---|---|
| (a) | |
| Water | to 100.000 |
| Caffeine BP - micronized (100% <15μ m*) | 10.000 |
| Potassium Sorbate | 0.150 |
| Nipastat | 0.150 |
| (b) Carbopol 940 | 0.400 |
| (c) | |
| Propylene Glycol | 5.000 |
| Glycerine | 5.000 |
| (d) Triethanolamine 99% | 0.800 |

*See Appendix for size distribution

Example 4

Caffeine Gel With Nonoxynol

|  | % |
|---|---|
| (a) | |
| Water - Deionised | 82.90 |
| Caffeine - micronized (100% <15μ m*) | 5.00 |
| Potassium Sorbate | 0.10 |
| Nipasept | 0.15 |
| (b) Carbopol 940 | 0.45 |
| (c) Propylene Glycol | 5.00 |
| (d) Nonoxynol | 6.00 |
| (e) Triethanolamine Special | 0.40 |

*See Appendix for size distribution

Application of the 10% gel product to the HSV lesions in accordance with the invention can be expected to deliver approximately 25 mg of caffeine.

SUMMARY

By way of summary:

(1) In two embodiments of the invention the use of wax-based formulations containing 5% and 10% caffeine in the form of a lipstick has been used by herpes labialis (cold-sore) sufferers as a preventive measure, especially during periods when cold sores are likely to occur. Incorporation of the caffeine in micronised form enhanced the effectiveness of the treatment.

This wax-based formula is easy and convenient to carry and apply and the formulation is designated to stay in situ for a period of time (i.e. longer than a normal solution of caffeine).

(2) In a third embodiment of the invention an adhesive type gel containing 10% caffeine has been developed for use in treating herpes simplex (both labialis and genitalis). This gel formula is designed for use in and around the lips but is equally suitable for application to the genital areas. A controlled study with a panel of herpes labialis sufferers has shown that a caffeine gel preparation reduces the time to healing compared to the previous sore when compared to similar patients treated with base gel.

An average of 2.5 days reduction in healing time occurred in the caffeine treated group. These findings strongly suggest that a gel formulation could be a useful preparation in the general management of patients with recurrent herpes labialis.

Appendix

Particle size distribution of micronised caffeine used in Examples

| Size microns | under | % in band | Size microns | under | % in band |
|---|---|---|---|---|---|
| 118.4 | 100.0 | 0.0 | 11.1 | 98.7 | 3.7 |
| 102.1 | 100.0 | 0.0 | 9.6 | 95.0 | 12.8 |

-continued

| Size microns | under | % in band | Size microns | under | % in band |
|---|---|---|---|---|---|
| 88.1 | 100.0 | 0.0 | 8.3 | 82.0 | 16.0 |
| 76.0 | 100.0 | 0.0 | 7.2 | 66.0 | 14.3 |
| 65.6 | 100.0 | 0.0 | 6.2 | 51.9 | 10.2 |
| 56.6 | 100.0 | 0.0 | 5.3 | 41.7 | 7.5 |
| 48.8 | 100.0 | 0.0 | 4.5 | 34.2 | 8.3 |
| 42.1 | 100.0 | 0.0 | 4.0 | 28.0 | 6.1 |
| 36.3 | 100.0 | 0.0 | 3.4 | 21.9 | 5.8 |
| 31.3 | 100.0 | 0.0 | 3.0 | 16.1 | 5.1 |
| 27.0 | 100.0 | 0.0 | 2.6 | 11.0 | 3.8 |
| 23.0 | 100.0 | 0.0 | 2.2 | 7.2 | 2.1 |
| 20.1 | 100.0 | 0.0 | 1.9 | 5.1 | 1.2 |
| 17.4 | 100.0 | 0.0 | 1.6 | 3.9 | 0.9 |
| 15.0 | 100.0 | <0.2 | 1.4 | 3.0 | 0.6 |
| 12.9 | 99.8 | 1.1 | 1.2 | 2.4 | |

Result source = sample
Record = 0
Focal length = 63 mm
Experiment type oil
Volume distribution
Beam length 14.2 mm
Obscuration 0.296
Volume conc = 0.0031
Log Diff = 4.65
Model indp
D(v.0.5) = 6.0μ
D(v.0.9) = 9.0μ
D(v.0.1) = 2.5μ
D(4.3) = 5.8μ
D(3.2) = 4.2μ
Span = 1.1
Spec surf area
1.4687 sq m/cc

I claim:

1. A pharmaceutical composition for topical use in the treatment of infections with Herpes virus, comprising as active ingredient an effective concentration of caffeine in the range from 8–12% and a pharmaceutically acceptable excipient suitable for topical administration, wherein said caffeine has a particle size distribution in which at least 90% of the particles have a mass median diameter (MMD) less than 9 μm in size.

2. A composition according to claim 1 wherein said excipient is selected to promote local retention of the active ingredient.

3. A composition according to claim 2 wherein said excipient is lipophillic.

4. A composition according to claim 1 in the form of a solid shaped body suitable for applying a film of the composition to the skin surface to be treated.

5. A composition according to claim 4 in the form of a lip-stick.

6. A composition according to claim 1 in the form of a gel.

7. A composition according to claim 1 wherein the particles have an MMD of 4–8 μm.

8. A method of treating a patient suffering from a Herpes infection in a tissue area, comprising topical application to said area of a pharmaceutical composition comprising as active ingredient an effective concentration of caffeine in the range from 8 to 12% and a pharmaceutically acceptable excipient suitable for topical administration, wherein said caffeine has a particle size distribution wherein the particles are less than 50 μm in size.

9. A method of treating a patient suffering from a Herpes infection in a tissue area, comprising topical application to said area of a pharmaceutical composition comprising as active ingredient an effective concentration of caffeine in the range from 8–12% and a pharmaceutically acceptable excipient suitable for topical administration, wherein said caffeine has a particle size distribution in which at least 90% of the particles are less than 9 μm in size.

* * * * *